United States Patent
Rongier et al.

(10) Patent No.: US 6,464,938 B1
(45) Date of Patent: Oct. 15, 2002

(54) DEVICE FOR MEASURING THE CONCENTRATION OF HYDROGEN IN A GASEOUS MIXTURE

(75) Inventors: Pierre Rongier, Vinon; Thierry Bonhomme, Lambesc; Christian Perez, Villeneuve, all of (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/743,816

(22) PCT Filed: May 26, 2000

(86) PCT No.: PCT/FR00/01431

§ 371 (c)(1),
(2), (4) Date: Jan. 11, 2001

(87) PCT Pub. No.: WO00/73775

PCT Pub. Date: Dec. 7, 2000

(30) Foreign Application Priority Data

May 28, 1999 (FR) ............................................ 99 06782

(51) Int. Cl.⁷ .............................................. G01N 33/00
(52) U.S. Cl. ..................... 422/51; 436/143; 436/144; 422/90; 422/83
(58) Field of Search ................. 436/143, 144; 422/51, 90, 83; 205/783; 73/25.03

(56) References Cited

U.S. PATENT DOCUMENTS

| | | | |
|---|---|---|---|
| 3,927,555 A | * 12/1975 | Godwin et al. | ............ 73/31.01 |
| 4,298,574 A | 11/1981 | Bohl | |
| 5,756,878 A | * 5/1998 | Muto et al. | ................. 73/25.03 |
| 5,959,190 A | 9/1999 | Peinecke et al. | |
| 6,242,263 B1 | * 6/2001 | Faber et al. | ................ 436/143 |

FOREIGN PATENT DOCUMENTS

| | | |
|---|---|---|
| DE | 4317568 A1 | 12/1994 |
| DE | 4317568 | 12/1994 |
| DE | 19645694 A1 | 5/1998 |

OTHER PUBLICATIONS

W. L. Gardner, "Sensor for Measuring the Atomic Fraction in Highly Dissociated hydrogen" Journal of Vaccum Science & Technology, Part A, U.S., American Institute of Physics, New York, vol. 13, No. 3, Part 1, May 1, 1995, pp. 763–766.
"Improved 02/H2 Gas–Mixture Sensor" NTIS Tech. Notes, vol. 7, No. J, 1984, pp. 509–510, U.S. Department of Commerce, Springfield, VA, ISSN: 0889–8464.

* cited by examiner

Primary Examiner—Jill Warden
Assistant Examiner—Sam Siefke
(74) Attorney, Agent, or Firm—Harness, Dickey & Pierce P.L.C.

(57) ABSTRACT

The present invention relates to a device for measuring the concentration of hydrogen in a gaseous mixture and in particular in the air constituting, for example, the atmosphere inside a closed premises. This device comprises a sensor in contact with a gaseous mixture, the sensor being linked to calculating and display function. The sensor comprises a catalyst capable of provoking an exothermic reaction with the hydrogen contained in the gaseous mixture, a conducting function fixed to the catalyst for transferring essentially by conduction the thermal energy release by the reaction from the catalyst to a cold point, a function for measuring the temperature T1 of the catalyst and the temperature T2 of the cold point being linked to the function for calculating the value of the molar concentration of hydrogen in a gaseous mixture from the temperature gradient measured T1–T2.

12 Claims, 2 Drawing Sheets

DEVICE FOR MEASURING THE CONCENTRATION OF HYDROGEN IN A GASEOUS MIXTURE

The present invention relates to a device for measuring the concentration of hydrogen in a gaseous mixture and in particular in the air constituting, for example, the atmosphere inside closed premises.

The technical field of the invention can perhaps be described as that of measurement, that is to say the quantitative evaluation of the concentration or level of hydrogen $H_2$ in a gaseous mixture such as air and water vapour; this atmosphere can also be charged with aerosols and dust, following an accident.

The devices or apparatus making it possible to ensure a qualitative or quantitative measurement of the hydrogen in a gaseous mixture can in fact be classified, on the one hand among detectors which can possibly be calibrated as measuring instruments within a very limited range of values, and on the other hand among laboratory apparatuses which are very complex and which require diverse supplies of reference gas as well as specialised operators.

These also exist indicators which are not usable at present in an atmosphere after an accident and whose range of uncertainty is very wide.

The simplest indicators are catharometers whose principle is based on measuring the thermal conductivity of the gas contained in a chamber.

Apparatuses like this are generally only used in an atmosphere of a known type and they are therefore calibrated specially with this aim. They also require a complex installation with gas sampling, a condenser and filters.

Recently, that is to say over about five years, a big demand has built up for measuring instruments able to be placed at precisely the point where the hydrogen level needs to be known, and capable of measuring hydrogen levels in a range from 0 to 30% of $H_2$, that is to say much above the ignition, combustion and explosion thresholds for hydrogen.

These demands result principally from operators of nuclear power plants world-wide. One of the major risks in the event of an accident causing fusion of the core is in fact the risk of explosion due to hydrogen, which means that each reactor requires the operation of several dozens of instruments.

Several types of measuring instruments trying to respond to the demands described above have therefore been developed and marketed. These measuring instruments depend on either the electrochemical or the thermal properties of hydrogen.

All these instruments have the radical inconvenience of requiring a permanent and substantial electricity supply whereas, in the event of a serious accident, the first consequence of this is precisely the loss of all electricity supplies.

The present inventors have moreover demonstrated, during tests concerning all the measuring instruments currently available, that none of them is acceptable, one of the fundamental reasons being that the atmosphere in the dome of a nuclear power plant after an accident comprises a very high proportion of water vapour and very high radioactivity under the form, among others, of aerosols and dusts, which disturb measuring systems.

The apparatuses known in the present state of the art also suffer from their weight, their dimensions, and their high cost.

In conclusion, all these instruments, whatever their type, have the inconvenience of a very high cost, lack of adaptation to the expressed demand and are, in short, little or not at all operational.

Therefore a need exists for a device for measuring the concentration of hydrogen in a gaseous mixture which, among other requirements, is simple, not bulky, light in weight and also highly reliable.

There is still a need for a device which makes it possible to measure with precision the concentrations of hydrogen in all the possible ranges of concentration, in particular those above the ignition, combustion and explosion thresholds for hydrogen.

This device must, in addition, be able to be used without suffering any disturbance for measuring the concentration of hydrogen for any gaseous mixture, whatsoever its composition, the possible presence of aerosols and dust, and its radioactivity, which is the case for example in the atmosphere present in the dome of a nuclear power plant after an accident.

The aim of the present invention is to provide a device for measuring the concentration of hydrogen in a gaseous mixture that responds, among other things, to the essential part of the needs indicated above.

The aim of the present invention is also to provide a device which does not have the inconveniences, limitations, lacks and disadvantages of the devices of prior art and which solves the problems of prior art mentioned above.

This aim is attained, in conformity with the present invention, by a device for measuring the concentration of hydrogen in a gaseous mixture comprising a sensor in contact with said gaseous mixture, said sensor being linked to means for calculation and display, in which said sensor comprises a catalyst capable of initiating an exothermic reaction with the hydrogen contained in the gaseous mixture, conducting means fixed to said catalyst to transfer the thermal energy generated, essentially by conduction, from said catalyst to a cold point, means for measuring the temperature T1 of said catalyst and the temperature T2 of said cold point being linked to means for calculating the value of the molar concentration of hydrogen in a gaseous mixture from the temperature gradient measured T1–T2, said means of calculation communicating said value of hydrogen concentration to said display means.

The device according to the invention responds to all the requirements indicated above, and provides a solution to the problems of prior art.

Generally speaking, the device according to the invention has much smaller dimensions and much lower weight compared to known devices.

In addition, as an example, the "sensor" device according to the invention can have overall dimensions of 10 to 15 cm and a weight generally less than 1 kilogram.

The low weight and small dimensions of the device according to the invention make it possible in a particularly advantageous manner to position it in places with particularly difficult access, which is not the case for the devices proposed at present.

In the same way, the device according to the invention is very simple, and only comprises a limited number of elements, which reduces the cost, simplifies manufacture and maintenance, and contributes to its reliability.

The sensor of the device according to the invention does not need any electricity supply, contrary to prior art devices, which require a permanent and substantial electricity supply.

In fact, the sensor only comprises elements which themselves generate the energies and electrical voltages needed.

This sensor autonomy makes it particularly adapted to operating in the chambers of nuclear power plants after an accident, since it can remain operational even if the electricity supply systems of the power plant fail.

Only the means for calculation and display, which can be moved outside the dangerous zone, are supplied electrically; but their consumption remains very low and their supply can be independent from the general supply of the power plant.

Thus, the battery life of the device according to the invention can be 10 to 100 times greater than the autonomy of prior art devices.

Moreover, the need for supply and/or remote control of the pumps and solenoid valves of prior art devices greatly increases the probability of very quick failure of one of the elements in an accident sequence.

Besides this, according to the invention, these means of calculation and display of the concentration of $H_2$ can be set at any distance from the sensor, that is to say that they can, for example, be placed outside the atmosphere of the power plant and not be submitted to the drawbacks of an accident situation.

The sensor and the means of calculation and display are linked by any known means such as a single cable whose dimensions are small and whose protection against aggression is greatly simplified.

In particular, the invention relies on the surprising and unexpected use of a catalytic exothermic reaction of hydrogen, for example the catalytic exothermic reaction of hydrogen with the oxygen in the air contained in a gaseous mixture, to transform the energy produced by this reaction into an element for measuring the concentration of $H_2$ which is, among other things, simple, reliable, and does not require electrical energy.

The use of these catalysts for such an aim is totally unexpected and the basic measuring principle according to the invention is totally different from that of prior art devices in which measurement of the level of $H_2$ is carried out essentially by following the variations of the electrochemical or thermal properties of hydrogen.

It has been demonstrated that the device according to the invention, in which the sensor essentially comprises a catalyst of the type described above can take reliable and precise measurements, whatsoever the composition of the gaseous mixture, such as air, and whatsoever the concentration of hydrogen, even at a high level.

In a particularly advantageous way, contrary to the prior art devices comprising a sensor operating on a different principle, the device according to the invention is not disturbed by aerosols, dusts or water vapour contained in the gaseous mixture, or by its radioactivity.

In fact, the catalysts of the sensor according to the invention are not "poisoned" by aerosols and dusts, and the water vapour associated with them, often in high quantity, does not disturb their operation, and neither does radioactivity.

The measuring device according to the invention—because of its principle property, the use of a catalyst—thus overcomes the main part of the problems encountered in prior art devices, particularly in the case of devices used in the atmosphere after nuclear power plant accidents.

The catalyst used in the sensor of the device according to the invention is preferably chosen from among the catalysts called "recombination" catalysts, that is to say catalysts which provoke the recombination of hydrogen and oxygen to form $H_2O$.

The use of such catalysts within the framework of a measuring device is neither described nor suggested in prior art.

Said recombination catalyst is chosen preferably from among platinum and palladium.

It is the considerable exothermic energy created by the reaction with the catalyst, for example by the recombination reaction, which leads to a rise in temperature of the catalyst (up to temperature T1), and the thermal gradient T1–T2 (where T2 is generally close to the ambient temperature) can be used for the measurement of the concentration of hydrogen.

The device according to the invention also provides a control adapted to the thermal gradients created by the exothermic phenomenon described above, which prevents the catalysts from initiating ignition of the hydrogen, as is the case for "recombiner" catalysts.

According to the invention, the thermal energy produced by the catalytic reaction is channelled towards a cold point, on the one hand in such a way as to avoid the temperature rising too high and to avoid any risk of ignition of the air and hydrogen mixture, and on the other hand in such a way as to make use of a parameter T1–T2 (T1 representing the temperature of the catalyst consecutive to the exothermic reaction and T2 representing the temperature of the cold point) proportional to the energy released.

According to the invention, said cold point to which the energy from catalysis is channelled is constituted of any appropriate means, preferably a cooling fin, whose temperature is generally close to the ambient temperature.

Moreover, advantageously, the sensor according to the invention is placed in a duct or chimney with which it is integral and in which the gaseous mixture circulates. The sensor, in the case where the measurement is to be made in an agitated atmosphere, for example the atmosphere after an accident in a nuclear power plant, is thus protected from aerodynamic turbulence, local heterogeneities and any possible direct spray of water on the catalyst.

In the duct or chimney, which is generally tubular, the sensor establishes a convection current which it controls itself by behaving as a sort of pump.

Preferably, said duct or chimney has small dimensions, that is to say that it is, for example in the shape of a tube or cylinder of a length of 10 to 15 cm and with a diameter of 2 to 3 cm. This duct can also have a rectangular cross-section, for example with dimensions 1.5×3 cm, and a length of, for example, 10 to 15 cm. The duct or chimney thus plays only a small role in the space required for the sensor, which can be set in places normally inaccessible to other sensors.

According to the invention, the transfer of energy between the hot point (catalyst at temperature T1) of the sensor and the cold point (cooling fin at temperature T2) is carried out essentially by conduction.

According to the formula (1) for thermal exchanges by conduction given below, the relation between the thermal gradient T1–T2 and the energy released is linear:

$$P(W)=((\lambda * S)/l)*(T1-T2) \qquad (1)$$

where:

l is the length of the conductor in cm;

S is the cross-section of the conductor in $cm^2$;

$\lambda$ is the conductivity of the material in $W.cm^{-1}.c^{-1}$.

Preferably, as indicated above, the chimney which is the part of the device with the biggest dimensions, is vertical and of rectangular cross-section.

The "sensor" part is generally perpendicular to the chimney and is generally of an external tubular or cylindrical shape.

The means of conduction are also generally in the shape of a tube or cylinder.

According to the invention, in order to encourage thermal exchanges by conduction, one reduces in an advantageous manner the thermal exchanges by radiation and by convection, which themselves are not linear.

Thus according to the invention and in order to reduce thermal exchanges by convection, said conducting means are enclosed in the sensor envelope and separated from it by a thickness of gas, such as air, sufficiently small for example 2 to 3 mm so that there are no thermal exchanges by convection in this space thus defined between the conducting means and the envelope.

In the same way, according to the invention, the surface of the catalyst is such that the catalytic energy (and thus the temperature of the conductor) is sufficiently low to make thermal exchanges by radiation negligible (in comparison to the thermal exchanges by conduction). The surface of the catalyst is thus a surface which can be described as small, that is to say about 1 cm$^2$ for example.

The device according to the invention also comprises means for measuring the temperature T1 of the catalyst (hot point), and the temperature T2 of the cold point. These means are generally constituted by thermocouples, which are generally connected head to tail and make it possible to provide directly and without cold soldering, a proportional measurement of the temperature gradient.

The device according to the invention comprises means for calculation and display of the molar hydrogen concentration, which are linked to said means for measuring the temperature.

In these means of calculation, the calculation of the molar hydrogen concentration is determined from the measurements of the temperatures T1 and T2.

The temperature gradient (T1–T2) is in fact the image of the partial pressure of hydrogen.

By definition, the $H_2$ molar concentration is given by the formula:

$$C(H_2)molar = ((H_2 \text{ partial pressure})/(\text{Ambient atmosphere total pressure})) * 100 \quad (2)$$

which can be written as:

$$C(H_2) = (P(H_2)/Pt) * 100 \quad (3)$$

The total pressure Pt is equal to the sum of the atmospheric pressure (Pa), the partial pressure of water vapour ($P(H_2O)$), and the partial pressure of hydrogen ($P(H_2)$) according to the equation:

$$Pt = Pa + P(H_2O) + P(H_2) \quad (4)$$

in which Pa=1; and $P(H_2)$ is given by the measurement of (T1–T2) by the intermediary of a transfer function which is a straight line (see for example FIG. 2).

For each sensor, it is generally necessary to carry out a preliminary calibration in order to obtain this transfer function or calibration curve, that is to say that each sensor is thus associated with its own calibration curve.

Nonetheless, this curve is the same for each type of catalyst. It is thus interesting to keep only a single type of catalyst. In this case, a stock of catalytic plates from a single manufacture will suffice for several years of supply.

This transfer function is introduced into the means of calculation.

In certain applications, the partial pressure of water vapour $PH_2O$ can be disregarded, so that the two means for measurement of the temperatures T1 and T2 are sufficient for defining $P(H_2)$ and Pt.

For example, in the case of a nuclear power plant, the ambient atmosphere, when there has been no accident, is air at atmospheric pressure.

The depression, which is of the order of a millibar can be disregarded, and the same applies to the partial pressure of water vapour which is of the order of 60% saturation at 25° C., that is less than 10 mbar.

Thus the atmosphere of origin can be assimilated to dry air at 1 bar.

Advantageously, according to the invention, in the case where the partial pressure of water vapour cannot be disregarded, it is then necessary to also envisage means of measurement of the ambient temperature T3, which can also take the form, for example, of a thermocouple and which are linked to said devices for calculation and display.

Thanks to this measurement of T3, one can determine the partial pressure $P(H_2O)$ with the help of saturation pressure tables, while $P(H_2)$ is determined as indicated above and Pa=1 bar, so one can easily deduce Pt in equation (4) and thus $C(H_2)$ in equation (3).

The tables giving $P(H_2O)$ in function of T3 are also introduced into the means of calculation.

For example, again in the case of an accident situation in a nuclear power plant, the atmosphere of the power plant is very quickly charged with water vapour, and the energy from this is such that it imposes a partial pressure of $H_2O$ equal to the saturation pressure at the new ambient temperature.

At the same time, there is generation of non-condensable hydrogen whose partial pressure adds to the two preceding pressures (for as a reminder, the detection of an accident situation provokes the sealed isolation of the power plant against the exterior), and Pt is determined by the equation (4) above, in which:

$P(H_2)$ is given by the response curve of the sensor by measurement of T1–T2;

$P(H_2O)$ is given by the tables of saturation pressure, by measurement of T3;

P(air) is taken to equal 1 bar.

In other utilisations of the device according to the invention, the user has to define the atmosphere of origin, and in an advantageous manner, according to the invention, the total pressure Pt of the gaseous mixture is then eventually measured by a pressure sensor.

This includes, for example, the case where the user does not want to disregard the partial pressure of other non-condensable gases not taken into account.

The characteristics and advantages of the invention will become clearer by reading the following description. This description, given as an illustrative but non-limiting example, refers to the attached drawings, in which:

Figure 1:
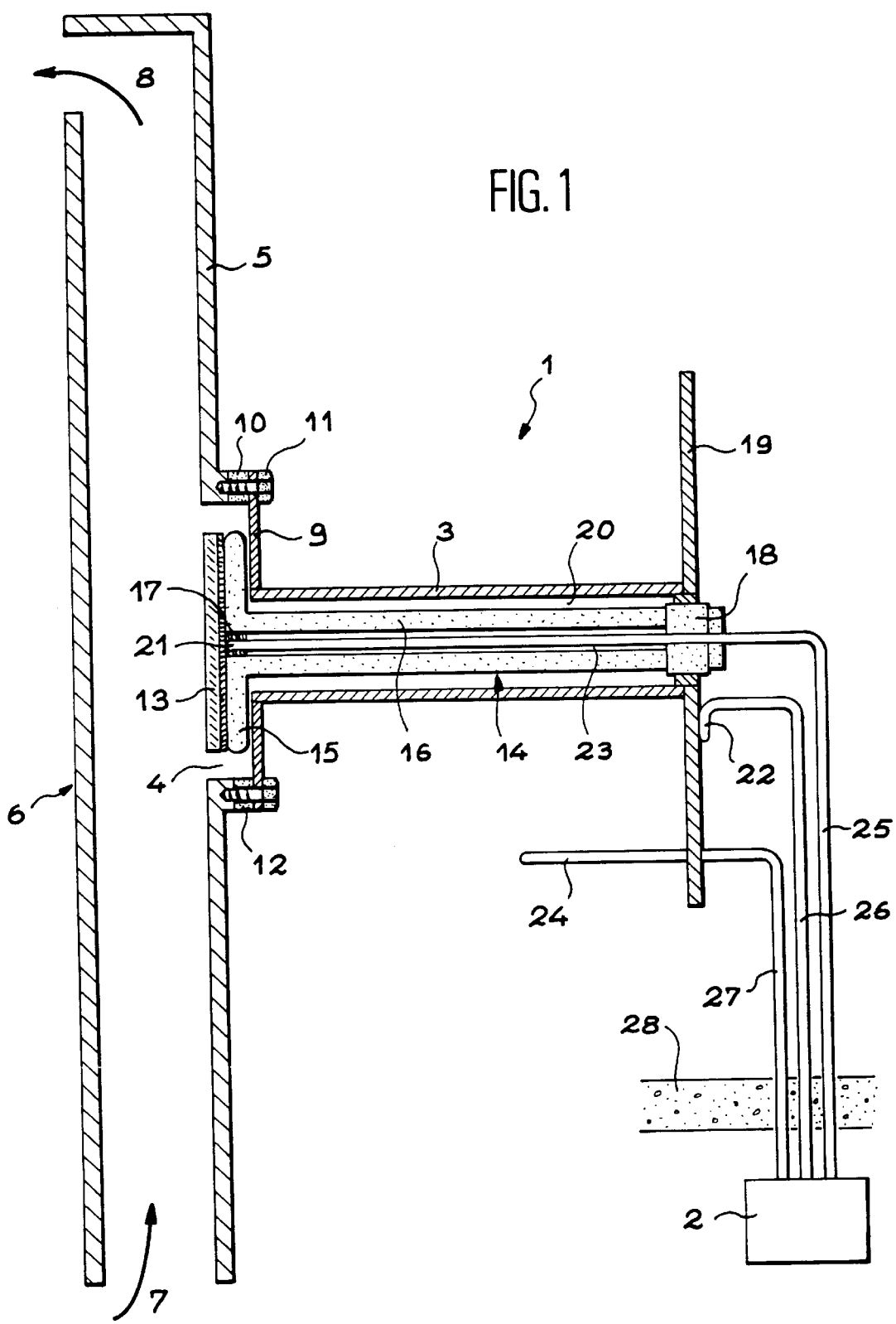
FIG. 1 represents a schematic view in cross-section of a measuring device according to the invention.

The sensor represented in FIG. 1 is approximately tubular in shape with an external envelope 3 constituted of a tube in a material such as stainless steel. The sensor, through the intermediary of this external envelope, is fixed in an orifice or piercing 4 made in the lateral wall 5 of a duct or chimney 6 which makes it possible to protect the sensor, in particular from aerodynamic turbulence, local heterogeneities and possible direct water spray on the sensitive organ of the sensor.

This chimney, which generally has the shape of a duct of rectangular cross-section, has small dimensions: for example a length of 10 to 15 cm and a cross-section of 1.5 to 3 cm.

The device according to the invention sets up a convection current in this chimney 6, on its own, which it controls by behaving as a sort of pump.

Thus, according to FIG. 1, the gaseous mixture enters the chimney 7 and leaves via the exit 8.

The chimney is generally made of a material such as stainless steel.

The fixation of the envelope of the sensor to the wall of the chimney is carried out through the intermediary of a part forming a flange 9, threadings 10 and nuts 11, a thermal insulator 12 being inserted between said envelope 3 and said wall 5.

It is to be noted that it is possible for this thermal insulator to be suppressed, the chimney then playing the role of cooling fin.

This thermal insulator is, for example in Teflon® and is in the form of a ring, for example with internal diameter of 2 cm, thickness 0.5 cm and width 1 cm.

The sensor, the essential element, comprises a catalyst 13 which, in FIG. 1, has the shape of a disc, of diameter 12 mm for example and a thickness of 0.1 to 0.2 mm.

The catalyst can also be of another shape, for example a square with sides of for example 12 mm.

A catalyst of such a size makes it possible to reduce thermal exchanges by radiation to a minimum. The catalyst is placed in the cut-out or orifice of the wall of the chimney, in such a way that it is in contact with the current of gaseous mixture circulating inside.

The catalyst is generally made of Pt and/or Pd generally set on an inert support of the oxide $Al_2O_3$ or another oxide.

The catalyst is fixed to a conducting element 14, generally comprising a first part forming the catalyst support, generally disc-shaped 15 of the same diameter as the catalyst, said first part being connected to a second part 16 of the element, generally in the form of an elongated tube, of length 2 to 4 cm, and with a smaller diameter than that of the first part generally disc shaped, that is to say from 4 to 5 mm.

The conducting element is generally made of stainless steel.

The fixation of the catalyst to said first part of the conductor is generally carried out by brazing 17; but a completely mechanical fixation can be envisaged in order to avoid this delicate operation.

The end 18 of said conducting tube opposite to the end supporting the catalyst constitutes the "cold point" of the sensor according to the invention.

In FIG. 1, this cold point is maintained at a temperature very close to ambient temperature by a cooling fin 19 fixed to said end 18 of the conducting tube and connected to the sensor envelope.

The dimensions of said fin are, for example, from 4 to 10 cm and are such that its temperature T2 does not go above ambient temperature by more than 5° C., this temperature must be sufficiently low so as not to produce too great a rise in temperature of the catalyst and conductor and so that the heat from the exothermic reaction is dissipated. The length of the conductor, which is between 2 and 4 cm is also chosen with this aim in mind.

Besides, in order to reduce or even annul convection exchanges, there is a space between the conducting element 14 and the envelope 3 of the sensor, separated by a thickness of gas 20 such as air, which must be as small as possible, for example from 2 to 3 mm.

The device according to the invention then comprises means for measuring the temperature of the catalyst T1, 21, and the temperature T2, 22, of the cold point, that is to say the temperature of the cooling fin.

These means are constituted, in FIG. 1, of thermocouples 21, 22 of the K type of a diameter of 1 mm, provided respectively in the proximity of the catalyst 13 and the cooling fin 19.

The thermocouple for measuring the temperature T1 of the catalyst is placed in a bore 23 of the conducting element of tubular shape in the immediate proximity of the catalyst, for example under the catalyst disc 13 and against the brazing 17.

Besides, the device shown in FIG. 1 comprises a third thermocouple 24 for measuring the ambient temperature T3.

The thermocouples 21, 22, 24, are linked by cables 25, 26, 27 to the calculation and display device 2. The three cables 25, 26, 27 can be grouped together to comprise just a single small diameter cable, for example with a diameter of less then 10 mm.

The length of said cable is not limited, so that the devices for display and calculation can be set in a position distant from the sensor, for example, in a position outside the chamber 28 in which the measurement is taken.

The display and measuring devices 2 are thus not exposed to the aggressive atmosphere to which the sensor is submitted, for example inside a nuclear power plant after an accident, and their operation can be autonomous, not needing a general supply from the said power plant.

The display and calculating means are classic devices, of small dimensions and low in cost. They can be supplied by an alternating current of 220V or by a direct current of 24V for reduced consumption, of the order of 20 W. The calculating device comprises, in particular, a memory in which the tables of pressure of saturated water vapour are stored, which makes it possible to calculate $P(H_2O)$ by introducing the value T3 of the ambient temperature. These memory means also store the curve giving the partial pressure of $H_2$ as a function of the temperature gradient T1–T2.

Figure 2:
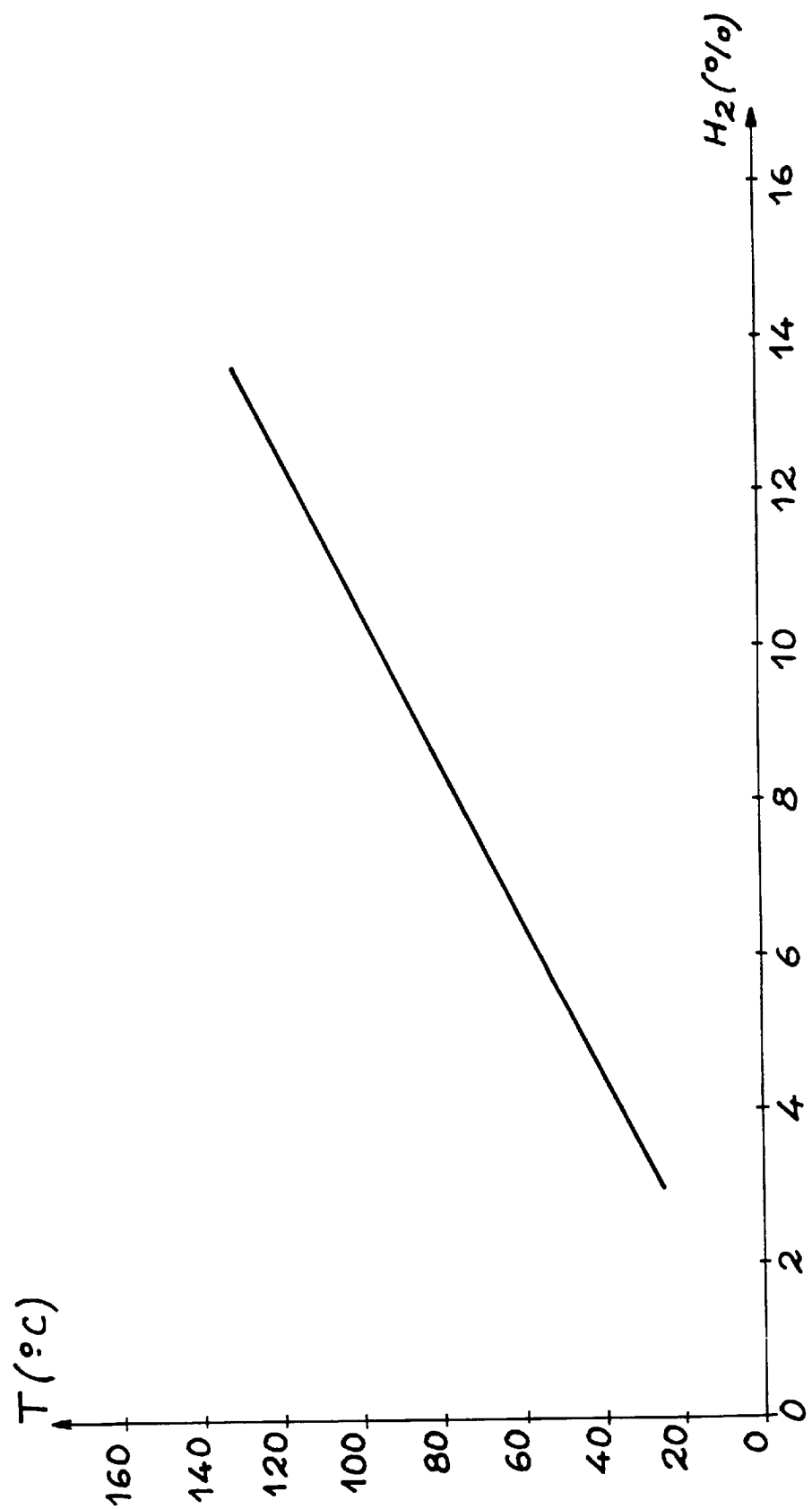
FIG. 2 is a curve giving the T1–T2 temperature (in ° C.) in function of the partial pressure of $H_2$ (%)In FIG. 1, a measuring device according to the invention is thus represented, this device comprising essentially a sensor 1 linked to a measuring and display device 2.

Such a curve is generally a straight line, for example, equation y=9.9754x−4.736, as is the case in FIG. 2.

By introducing the values of T1 and T2 from the measurement means into the calculation device, the latter calculates T1–T2, then $P(H_2)$, thanks to said straight line.

The calculation device 2 thus requires preliminary calibration per type of sensor, enabling it to calculate said transfer function or straight line specific to each type of sensor, which is then stored in the memory of said calculation device.

Next, the calculation device deduces the value of $C(H_2)$, this value being communicated to the display device, such as a screen . . . or other means of visualisation, and a device for a sound or luminous alarm can also be provided.

What is claimed is:

1. Device for measuring the concentration of hydrogen in a gaseous mixture comprising a sensor in contact with said gaseous mixture, said sensor being linked to calculating and display means, in which said sensor comprises a catalyst capable of provoking an exothermic reaction with the hydrogen contained in the gaseous mixture, conducting means fixed to said catalyst for transferring essentially by conduction the thermal energy released by said reaction from said catalyst to a cold point, means for measuring the temperature T1 of said catalyst and the temperature T2 of said cold point being linked to means for calculating the value of the molar concentration of hydrogen in the gaseous mixture from the temperature gradient measured T1–T2, said means of calculation communicating said value of hydrogen concentration to said display means;

wherein said cold point further comprises a cooling fin.

2. Device according to claim 1, in which said catalyst is chosen from among the recombination catalysts of oxygen and hydrogen.

3. Device according to claim 2, in which said catalyst is chosen from among platinum and palladium.

4. Device according to claim 1, in which said sensor is placed in a duct or chimney with which it is integral and in which the gaseous mixture circulates.

5. Device according to claim 1, in which the surface of the sensor is sufficiently small to make thermal exchanges by radiation negligible compared with thermal exchanges by conduction.

6. Device according to claim 1, in which said conducting means are surrounded by the envelope of the sensor and separated from it by a thickness of gas which is sufficiently small so that there are no thermal exchanges by convection in the space defined between the envelope and the conducting means.

7. Device according to claim 1 comprising, in addition, means for measurement of the ambient temperature $T3$.

8. Device according to claim 1 comprising, in addition, a pressure sensor to measure the total pressure $Pt$ of the gaseous mixture.

9. Device according to claim 1, in which said means for measuring the temperatures $T1$, $T2$ and $T3$ are constituted by thermocouples.

10. Device according to claim 9, in which said thermocouples for measuring the temperature $T1$ of the catalyst and the temperature $T2$ of the cold point are connected head to tail without cold welding.

11. A device for measuring a concentration of hydrogen in a gaseous mixture comprising:

a catalyst in contact with said gaseous mixture, said catalyst being adapted to provoke an exothermic reaction with the hydrogen contained in the gaseous mixture;

conducting means extending between said catalyst and a cold point for transferring essentially by conduction thermal energy released by said exothermic reaction from said catalyst to said cold point;

measuring means linked to said catalyst and said cold point for measuring a temperature $T1$ of said catalyst and a temperature $T2$ of said cold point;

calculating means linked to said measuring means for calculating a value of a molar concentration of hydrogen in the gaseous mixture from a temperature gradient measured $T1$–$T2$; and display means communicating with said calculating means for displaying said value of molar concentration of hydrogen;

wherein said cold point further comprises a cooling fin.

12. The device of claim 1 wherein said conducting means is coupled to said catalyst and said cooling fin.

* * * * *